United States Patent
Blakeley et al.

(10) Patent No.: US 8,216,183 B2
(45) Date of Patent: Jul. 10, 2012

(54) HEATING DEVICE

(75) Inventors: William Blakeley, Newry County Down (GB); Michael Lanigan, Newry County Down (GB); Lillian Cromie, Newry County Down (GB)

(73) Assignee: Norbrook Laboratories Limited, Newry, County Down (GB)

( * ) Notice: Subject to any disclaimer, the term of this patent is extended or adjusted under 35 U.S.C. 154(b) by 0 days.

(21) Appl. No.: 12/669,649

(22) PCT Filed: Jul. 21, 2008
(Under 37 CFR 1.47)

(86) PCT No.: PCT/GB2008/002507
§ 371 (c)(1),
(2), (4) Date: Nov. 10, 2010

(87) PCT Pub. No.: WO2009/013486
PCT Pub. Date: Jan. 29, 2009

(65) Prior Publication Data
US 2011/0166517 A1 Jul. 7, 2011

(30) Foreign Application Priority Data
Jul. 20, 2007 (GB) .................................. 0714243.3

(51) Int. Cl.
*A61F 7/12* (2006.01)
*F24J 1/00* (2006.01)
*F24J 3/00* (2006.01)

(52) U.S. Cl. .................................. 604/113; 126/263.08

(58) Field of Classification Search .................. 604/403, 604/407–416, 113; 126/263.01, 263.08; 383/110
See application file for complete search history.

(56) References Cited

U.S. PATENT DOCUMENTS

| 2,733,710 | A | * | 2/1956 | Zibell ....................... 126/263.01 |
| 3,587,934 | A | * | 6/1971 | Elmore .......................... 222/171 |
| 5,078,699 | A | * | 1/1992 | Haber et al. ................... 604/250 |
| 5,295,964 | A | | 3/1994 | Gauthier |
| 5,465,707 | A | * | 11/1995 | Fulcher et al. ........... 126/263.08 |
| 2003/0116452 | A1 | * | 6/2003 | Saric et al. ..................... 206/219 |
| 2005/0230376 | A1 | | 10/2005 | Gomez |

OTHER PUBLICATIONS

English Abstract Attached Apparatus Inventor: Passarello Paolo (IT) Publication WO2005056089 Priority Date: Dec. 5, 2003.
English Abstract Attached Warming Infusion Fluids Inventor: Marriott Cathryn Publication GB2248106 Priority Date: Aug. 9, 1990.
An English Abstract Was Not Available. Accordingly, an English translation of a first portion of the Description as provided by the EPO website is attached to the reference Infusions Inventor: Engel Joachim-Michael Publication DE2515889 Publication Date: Oct. 21, 1976.
PCT International Bureau, International Preliminary Report PCT/GB2008/002507, date of mailing Feb. 4, 2010.

* cited by examiner

*Primary Examiner* — Matthew F DeSanto
(74) *Attorney, Agent, or Firm* — Luedeka Neely Group, PC

(57) ABSTRACT

A heating device (1) is described for a container (7) of a liquid pharmaceutical product having a viscosity of 50-500 cP at 4° C. and contained within a glass container. The device (1) comprises a substantially rigid, thin-walled housing (2) defining an openable chamber for receiving the container (7), a heat source (6) in the chamber comprising a hermetically sealed package containing a super-cooled metal salt fluid or liquid and an actuator (14) for activating the super-cooled metal salt to produce heat, wherein the ratio of the volume of the metal salt to the intended volume of the product is no more than 1:1.

17 Claims, 3 Drawing Sheets

HEATING DEVICE

CROSS-REFERENCE TO RELATED APPLICATION

This application claims priority under all applicable statutes, and is a U.S. National phase (37 USC Section 371) of International Application PCT/GB2008/002507, filed Jul. 21, 2008, and entitled HEATING DEVICE, which claims priority to GB 0714243.3, filed Jul. 20, 2007, incorporated herein by reference in their entireties

FIELD OF THE INVENTION

The present invention relates to devices suitable for heating liquid pharmaceutical products for administration to animals, especially parenteral products that are ideally administered at temperatures close to room temperature (approximately 25° C.).

BACKGROUND

Heating of liquid pharmaceutical products (from herein referred to as "products") prior to administration is often required to increase the solubility of the active ingredients in these products. With specific regard to parenteral products, especially veterinary parenteral products, heating can also reduce the potential for systemic cold-shock to the patient upon administration of the product.

These products can often be administered in remote, exposed and cold conditions e.g. in fields where animals need to be treated. Therefore heating or resolubilisation of the product constituents is often carried out by shaking and rolling between the users hands or even using heating jackets around the bottle or container that require an external energy supply like a battery or sunlight. A considerable amount of energy and time can be expended trying to heat the liquid formulations to the required temperature. This problem is compounded by the volume of the bottles being in the range of 2000 to 100 ml in order to provide doses to a plurality of patients or animals as well as the fact that glass or plastic bottles several millimetres thick are routinely used as product packaging. Furthermore, many products for veterinary use are extremely viscous at e.g. about 50-500 cP at about 4° C.

Additionally such products, especially parenteral products, are commonly encased in protection chambers to minimise breakage. It is clearly not desirable to have yet another device in addition to the protection chamber for the user to handle prior to administration of the product. Therefore it is desirable to have a device that allows the user of the product to heat products without having to remove the product from the protection chamber.

Some heating devices for warming IV infusion products for administration to humans are known. For example, GB 2248106 and U.S. Pat. No. 4,934,336 show flexible insulating packs with warming devices for heating bags of fluid for IV infusion. However, the fluid is typically a liquid of very low viscosity compared with typical veterinary products, and it is contained within a thin-walled plastic bag. Such devices are therefore unsuitable for highly viscous veterinary products contained in comparatively thick-walled glass containers, because insufficient heating and protection against breakage is provided.

WO 2005/056089 describes a heating device for a rigid container of fluid, but the casing has extremely thick walls, making it heavy and bulky, and it requires an external power supply for heating. It is therefore entirely unsuitable for veterinary use where portability is essential.

STATEMENTS OF INVENTION

The present invention provides a heating device for a container of a liquid pharmaceutical product having a viscosity of 50-500 cP at 4° C. and contained in a glass container, comprising a substantially rigid, thin-walled housing defining an openable chamber for receiving the container, a heat source in the chamber comprising a hermetically sealed package containing a super-cooled metal salt fluid or liquid and an actuator for activating the super-cooled metal salt to produce heat, wherein the ratio of the volume of the metal salt to the intended volume of the product is no more than 1:1.

In this way, the invention provides a compact, self-contained and re-usable heating device.

Preferably, the heat source defines a cavity for receiving the container with a close fit, for most efficient heat transfer.

Conveniently, the actuator is integral with the heat source.

In one embodiment, the actuator comprises a flexible tab extending from the heat source.

Preferably, the actuator is positioned so as to be accessible when the container is received within the heat source and the housing is in an open position.

For ease of use, the housing may define an aperture for accessing the container for withdrawal of product therefrom without removal of the container from the housing.

The device may further comprise means to hold the heating device in use such that the container is inverted and product can be dispensed therefrom under gravity or other dispensing means.

In one example, the housing comprises a body and a removable lid, and the aperture is provided in the lid.

Preferably, the holding means comprises a hole in the base of the housing for receiving a hook to suspend the device in an inverted position.

The heating device may further comprise an insulating member located in the chamber between the walls of the chamber and the heat source.

The insulating member may be formed of one or more of cardboard, polypropylene, polystyrene and neoprene.

The super-cooled metal salt is preferably one or more of sodium acetate trihydrate, sodium borate and sodium thiophosphate and their respective hydrates.

The heating device may further comprise a protective cover for receiving the housing.

The heating device may also include tubing for connecting the container to a delivery device, wherein the tubing is provided with insulation. This may be integral with the tubing or a flexible sleeve removable locatable around the tubing.

In another aspect, the invention also provides apparatus for dispensing a liquid pharmaceutical product comprising a container of a liquid pharmaceutical product received within a heating device of the type described above, a support frame adapted to be worn on the user's back or shoulders and means to attach the heating device to the frame.

This allows the use to easily carry the device in a manner in which the product is available for dispensing.

The invention will now be described in detail, by way of example only and with reference to the accompanying drawings in which.

Figure 1:
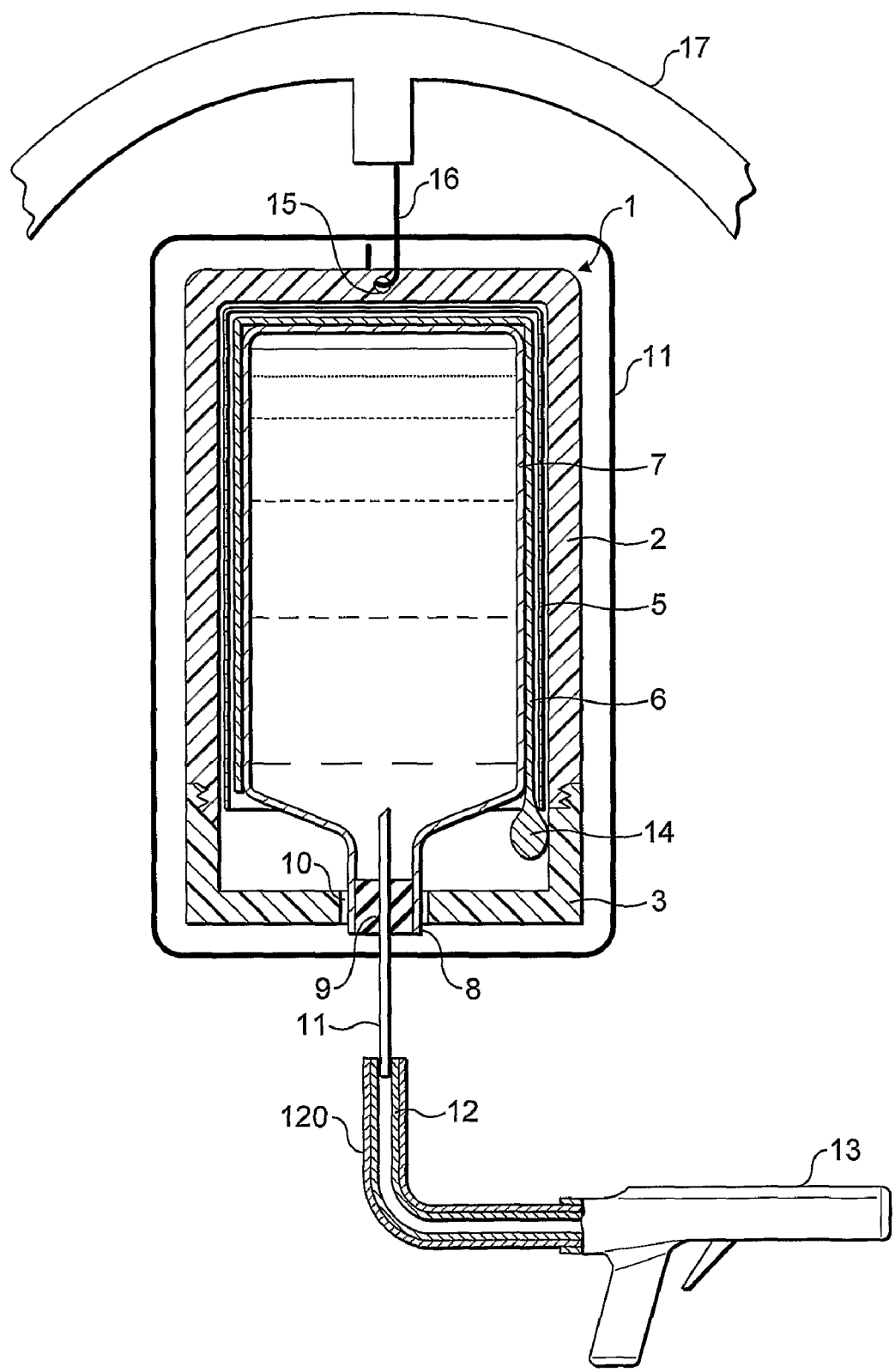
FIG. 1 shows a cross-section of one embodiment of the present invention, in an inverted position ready for use.
Figure 2:
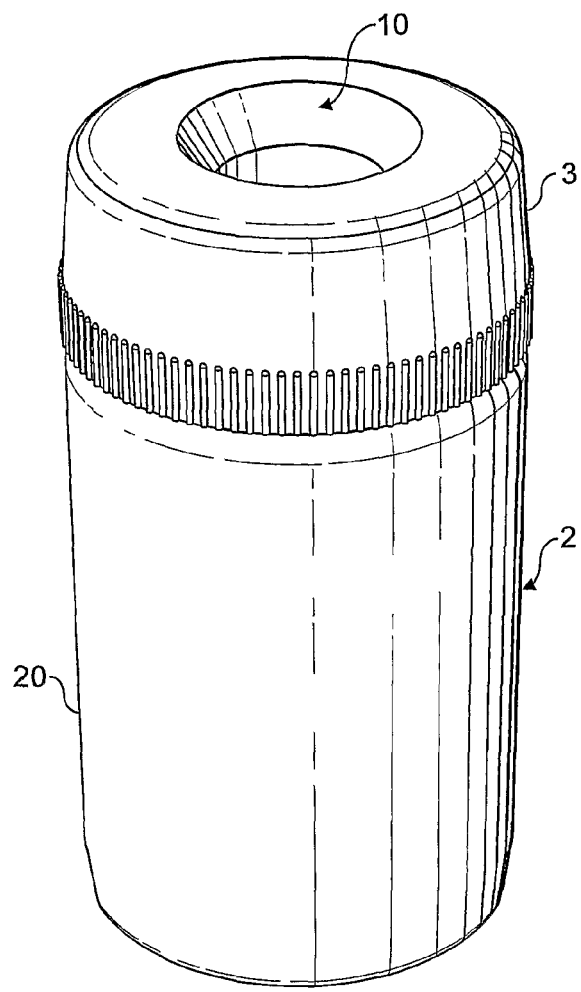
FIG. 2 is a perspective view of one embodiment of container for use in the present invention.

As shown in FIG. 1, the device 1 consists of an outer housing 2 with a removable lid 3, together defining a protection chamber 4.

Figure 3:
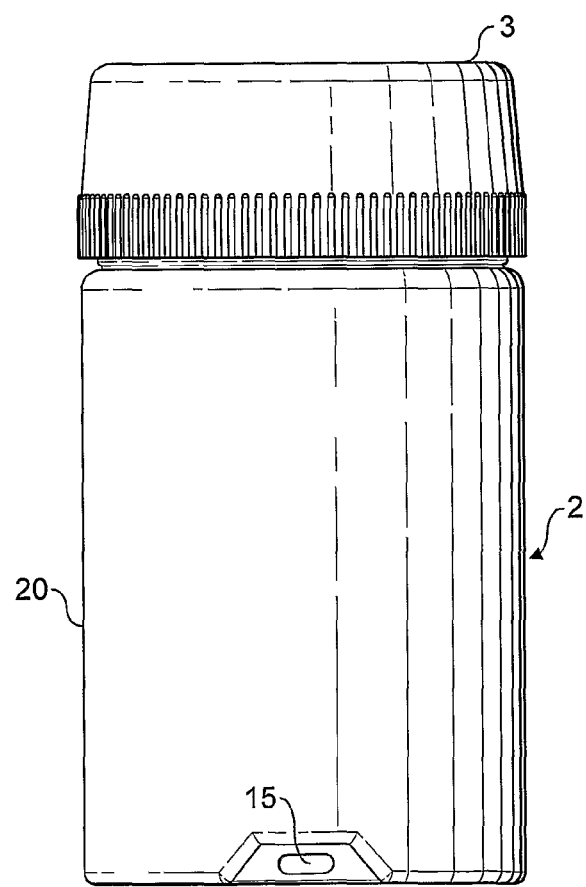
FIG. 3 is a side view of the container of FIG. 2.
Figure 4:
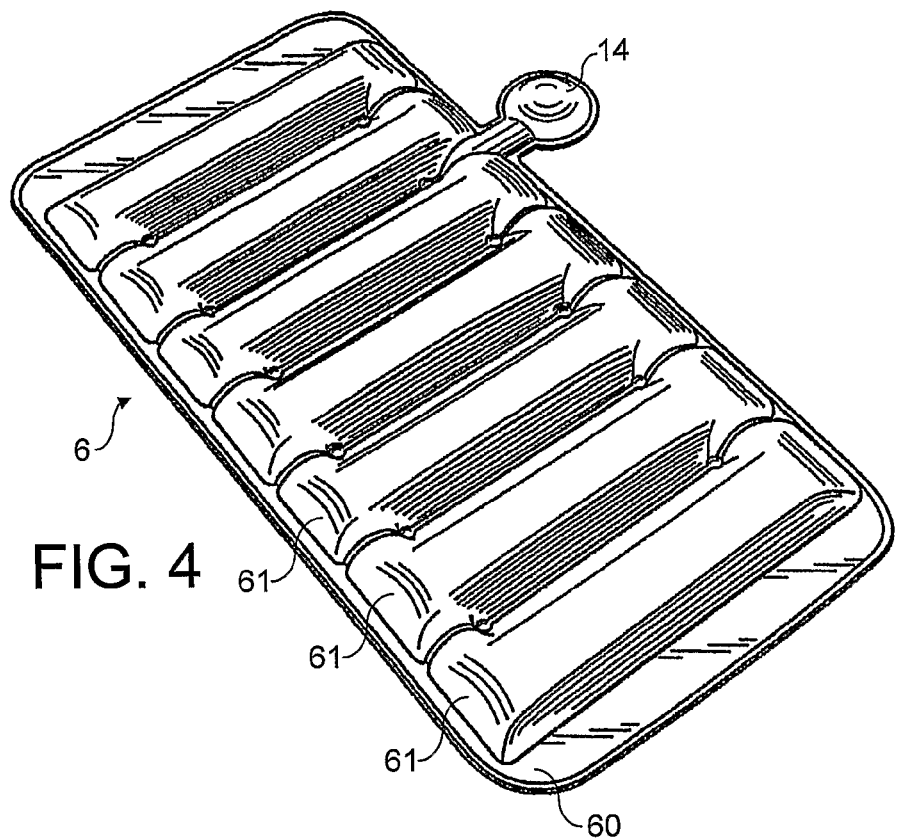
FIG. 4 is a perspective view of one embodiment of a heat source for use in the present invention, when flat.

One embodiment of the housing 2 is best seen in FIGS. 3 and 4. This housing 2 preferably comprises a hollow cylindrical body 20 with a removable lid 3. The lid 3 defines a central aperture 10 for accessing a bottle of pharmaceutical product held within the housing (as described further below). The body 20 and lid 3 are removably connectable to one another preferably via a screw thread, although a hinge or other connecting means could be used. The base of the body 20 includes a web defining a hole 15.

The housing 2 is preferably formed from a tough but lightweight material such as plastic, in particular, high density polyethylene. To receive a typical 500 ml bottle of pharmaceutical product having a diameter of approximately 7.5 cm and height of 18.5 cm, a typical housing 2 may have an outside diameter of about 11 cm, a height including the lid of about 20 cm. However, it would be a thin walled container, preferably having a wall thickness of around 1 mm. Accordingly, the housing 2 is not significantly larger than the bottle it is intended to receive, keeping the overall device 1 compact.

An insulating member 5 is received within the chamber 4. This is in the form of a cylindrical sleeve formed of an insulating material. It may be open at both ends, or as shown it may be closed at one end by a circular wall, to provide maximum insulation. The insulating member 5 may be formed of any suitable material such as corrugated cardboard, polystyrene or neoprene, etc. Preferably, in cross-section the insulating member 5 will include hollow cells or channels, as are present in corrugated cardboard or plastic, which trap air and provide maximum insulation, whilst still being a thin walled structure, for example around 2 mm in thickness. It will be appreciated that the walls of the housing 2 could themselves be formed from an insulating material so that use of a separate insulating member 5 would be unnecessary.

A heat source 6 (described further below) is received within the insulating member 5. This is also in the form of a cylindrical sleeve. It may be open at both ends, or as shown it may be closed at one end by a circular wall, to provide a larger surface area for transmitting heat.

A bottle 7 containing a liquid pharmaceutical product can be received within the heat source 6, preferably with a tight fit. Typically, the bottle 7 is of a type which narrows via shoulders to a neck 8 initially secured with a screw cap. In use, this may be replaced with a closure member such a bung 9 through which a needle 11 can penetrate in order to dispense the product. In use, the opening of the neck 8 of the bottle 7 is accessible via the aperture 10 formed in the lid 3 of the housing 2. The neck 8 may protrude slightly out of the housing 2 as illustrated in FIG. 1 or it may be approximately level with the top of the lid or slightly below.

Pharmaceutical product can be extracted from the bottle 7 by means of a hollow needle 11 penetrating the bung 9. The needle 11 may be in communication with tubing 12 leading to a delivery gun 13. The tubing 12 may itself be provided with insulation to maintain the elevated temperature of the pharmaceutical product as it is dispensed. The tubing 12 may simply have thick walls or some form of exterior insulating layer formed integrally with the tubing walls. Alternatively, a separate insulating sleeve 120 may be provided as shown in FIG. 1. Conveniently, this is in the form of a flexible sheet of insulating material which can be wrapped around the tubing 12 and secured in place, for example with hook and loop fasteners. Alternatively, the insulating sleeve 120 could also be of tubular form and sized to be slidable over the tubing 12 before it is connected to the needle 11 and/or the delivery gun 13.

The base of the housing 2 preferably includes an attachment means, shown here in a form of the hole 15, allowing the device 1 to be hung, inverted as shown, from a hook 16 on a brace 17. This allows the device 1 to be hung over user's back or shoulders so that the product flows from the bottle to the delivery gun 13, and the user is free to move around to administer the product. The entire device 1 may be contained within a protective bag or cover 18 such as flexible waterproof bag.

Figure 5:
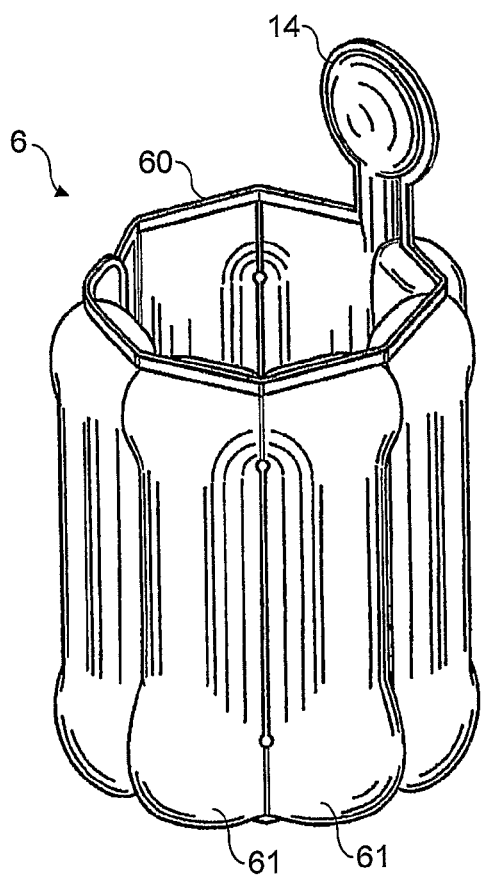
FIG. 5 is a perspective view of the heat source of FIG. 4 when assembled into a cylindrical form for insertion into the container.

The heat source 6 is in the form of a hermetically sealed bag or package 60 containing a rechargeable heat source such as super-cooled metal salt fluid or liquid. The metal salt may be one or more of sodium acetate, sodium borate and sodium thiophosphate and their respective hydrates. The bag 60 may be formed as a generally flat member as shown in FIG. 4 which can be bent round to form a cylinder and fastened in that position as shown in FIG. 5. The bag 60 may be subdivided into a series of compartments 61 to facilitate bending it into the cylindrical form.

An actuating member 14 in the form of an enlarged tab extends from the main body of the heat source 6. In use, this tab 14 extends into the part of the chamber 4 defined by the lid 3, so that the actuating member 14 is accessible above the shoulders of the bottle 7.

The actuating member 14 is in the form of a flexible tab that a user can grasp between thumb and finger and flex back and forth. This action creates vibrations in the super-cooled fluid or liquid to initiate an exothermic crystallisation of the metal salts in a known manner, (see for example U.S. Pat. No. 4,077,390).

The heat source 6 can be recharged by heating, to enable multiple uses. Typically, recharging is effected by placing the heat source 6 into boiling water for a period of time, usually in the order of 5 to 15 minutes, or as long as necessary to completely resolubilise the crystallised metal salts.

The heat source 6 will be dimensioned so that its inside diameter is a tight fit around a bottle 7 of given volume, whilst the outside diameter is a tight fit within the insulating member 5 in the housing 2. The volume of fluid or liquid contained within the bag 60 should be approximately equal to or less than the volume of pharmaceutical product held in the bottle 7 so that the ratio of the volume of the heat source 6 to the volume of the pharmaceutical product is no more than 1:1. For a typical 500 ml bottle of pharmaceutical product with typical dimensions as mentioned earlier, the heat source may have a height of approximately 15 cm and a maximum wall thickness of around 1 to 1.5 cm.

The heating device 1 is particularly useful for a pharmaceutical liquid product that is viscous at or below room temperature, and which is suitable for parenteral administration, and for multiple dose veterinary applications.

In particular, the heating device 1 is intended for use with pharmaceutical liquid products that have a viscosity in the range 50-500 cP at 4° C.

Typically, the pharmaceutical liquid product comprises an antimicrobial selected from the list comprising tetracyclines such as oxytetracycline, cephalosporins, penicillins such as ampicillin, amoxycillin, penicillin G or a phenciol like thiamphenicol, chloropamphenicol or florfenciol, or macrolides such as erythromycin, tylosin, tilmicosin or aminoglycosides such as dihydrostreptomycin or a quinolone or a sulphonamide or a diaminopyrimidine e.g., trimethoprim, either alone or in combination.

The antimicrobial active ingredient of the pharmaceutical liquid product may be admixed with an non-steroidal anti-inflammatory selected from the list comprising indolines such as indomethacin, salicylates such as aspirin, oxicams such as piroxicam and meloxicam, acetic acid such as diclofenac, fenamates such as tolfenamic acid and flunixin, propionic acids such as ketoprofen, ibuprofen and carprofen, para amino phenol derivatives such as acctaminophen, pyrazoles such as phenylbutazone, sulphonanilides such as nimesulide, or other such drugs with anti-inflammatory activity.

In particular, the pharmaceutical liquid product may be a long acting oxytetracycline, a long acting oxytetracycline in intimate ad mixture with flunixin, a long acting florfenicol or a long acting florfenicol in intimate admixture with flunixin.

The pharmaceutical liquid product may comprise an anthelmintic active, which can be a milbemycin oxime or a macrocyclic lactone. The anthelmintic active ingredient may be an avermectin, ivermectin, doramectin, moxidectin or selamectin, and may be admixed with an anti-parasitic agent.

The anti-parasitic agent of the pharmaceutical liquid product may be a salicylanilide such as closantel.

Typically such pharmaceutical products are supplied in volumes ranging from 5000 ml down to 100 ml, in appropriately sized bottles. Specifically, the volume may be 2000 ml, 1000 ml, 500 ml or 250 ml. The heating device and its various components will be made to suitable dimensions to receive a bottle of the desired volume. The device may be manufactured in a range of sizes to suit different bottles. Alternatively, the heat source 6 may be adjustable. For example, when formed as a flat bag which can be folded into a cylindrical form, it may be provided with fastening means at different locations to enable it to form cylinders of differing diameter. In another alternative, a larger size of heat source 6 could be replaced with a smaller size, with a thicker insulating member 5, or more than one insulating member 5, being used to fill any resulting gap between the walls of the chamber 2 and the heat source 6.

In one example of use of the device, the pharmaceutical liquid product comprises avermectin and closantel, for example Closamectin® (see patent EP1478372B).

To illustrate how the device 1 works in practice, experiments were conducted in which a 500 ml bottle of Closamectin® was placed into the chamber 4, with a cardboard insulating member 5 placed between the heat source 6 and the internal walls of the chamber 4. Closamectin® was chosen as a model product.

The fit was sufficiently tight to ensure maximum contact between the heat source and the external surface of the Closamectin® bottle 7 as well as reduce heat loss from the chamber 4 and allow removal of the bottle 7 without too much resistance.

In repeated experiments (n=4) the Closamectin® bottle 7 was initially at 4° C., the ambient temperature was also 4° C. and the actuator was pressed at 0 minutes. Every 5 to 10 minutes a temperature reading was taken. The results are displayed in Table 1 below.

TABLE 1

| Time (minutes) | Temperature (Degrees Celcius) |
| --- | --- |
| 0 | 4 |
| 5 | 8 |

TABLE 1-continued

| Time (minutes) | Temperature (Degrees Celcius) |
| --- | --- |
| 10 | 14.5 |
| 15 | 19.5 |
| 20 | 21.5 |
| 30 | 23.6 |
| 40 | 24 |
| 50 | 24 |
| 60 | 24 |

This shows how the device of the present invention is able to heat the volume of pharmaceutical product in use.

In particular, these tests show that the device of the present invention is able to raise the temperature of the pharmaceutical product by at least 10° C. in only 10 minutes. Thus, the time taken to raise the temperature by a satisfactory amount is not excessive.

It will noted that even after 60 minutes of heating, the temperature of the product does not exceed about 25° C., even though the heat source is in itself capable of reaching a temperature of around 50° C. Thus, the device of the present invention ensures that the product temperature is not raised too much and does not risk causing the animal any discomfort or harm by providing a product for injection that is too hot.

In addition, drop tests were carried out to establish the safety of the device in typical use and the risk of breakage of the bottle 7 if the device is dropped. 500 ml bottles of pharmaceutical product were used for this test, placed within the housing 2, together with the insulating member 5 and heat source 6. 20 bottles were tested, each being dropped 10 times from a height of approximately 1.2 metres. No breakages of the bottles occurred.

Thus, the combination of the housing 2, insulating member 5 and heat source 6 not only provide the ability to heat a very viscous product with a viscosity of 50-500 cP at 4° C. to a sufficiently high temperature within a comparatively short time, but also provides superior physical protection to the bottle of pharmaceutical product, as compared with the housing alone or a bottle contained only in a flexible insulating bag. Furthermore, the device of the present invention provides these advantages while having a ratio of the volume of the heat source to the volume of the pharmaceutical product of no more than 1:1. Therefore the device is not excessively bulky or heavy and does not significantly increase the overall size and weight of the end product to be handled by a vet.

Thus, the present invention provides a lightweight, self-contained and reusable heating device for heating containers of pharmaceutical products. It requires no external power source and is sufficiently compact and lightweight to be carried by a user without significantly hindering their mobility or their ability to administer the product. It can also be re-charged for use multiple times. It will be appreciated that various alterations or modifications could be made to the device without parting from the scope of the claims.

The invention claimed is:

1. A heating device for a container of a liquid pharmaceutical product having a viscosity of 50-500 cP at 4° C. and contained within a glass container, comprising a rigid, thin-walled housing defining an openable chamber for receiving the container, the housing including an open end, a closed end, and a closure member operable for opening and closing of the housing for access to the chamber, a heat source in the chamber comprising a hermetically sealed package containing a super-cooled metal salt fluid or liquid and an actuator for activating the super-cooled metal salt to produce heat, wherein the ratio of the volume of the metal salt to the intended volume of the product is no more than 1:1, and wherein the volume of product is from 100 ml to 5000 ml and wherein the actuator is positioned so as to be accessible through the open end when the container is received within the heat source and the housing is open.

2. A heating device as claimed in claim 1, wherein the housing defines an aperture for accessing the container for withdrawal of product therefrom without removal of the container from the housing.

3. A heating device as claimed in claim 2, wherein the closure member comprises a removable lid, and wherein the aperture is provided in the lid.

4. A heating device as claimed in claim 3, wherein the holding means comprises a hole in the base of the housing for receiving a hook to suspend the device in an inverted position.

5. A heating device as claimed in claim 2, further comprising means to hold the heating device in use such that the container is inverted and product can be dispensed therefrom under gravity or other dispensing means.

6. The heating device as claimed in claim 1, further comprising tubing for connecting the container to a delivery device, wherein the tubing is provided with insulation.

7. The heating device as claimed in claim 6, wherein the insulation is integral with the tubing.

8. A heating device as claimed in claim 6, wherein the insulation comprises a flexible sleeve removably locatable around the tubing.

9. A heating device as claimed in claim 1, wherein the actuator is integral with the heat source.

10. A heating device as claimed in claim 9, wherein the actuator comprises a flexible tab extending from the heat source.

11. A heating device as claimed in claim 1, further comprising an insulating member located in the chamber between the walls of the chamber and the heat source.

12. A heating device as claimed in claim 11, wherein the insulating member is formed of one or more of cardboard, polypropylene, polystyrene and neoprene.

13. A heating device as claimed in claim 1, wherein the heat source defines a cavity for receiving the container with a close fit.

14. A heating device as claimed in claim 1, wherein the super-cooled metal salt is one or more of sodium acetate, sodium borate and sodium thiophosphate and their respective hydrates.

15. A heating device as claimed in claim 1, further comprising a protective cover for receiving the housing.

16. Apparatus for dispensing a liquid pharmaceutical product comprising a container of a liquid pharmaceutical product received within a heating device as claimed in claim 1, a support frame adapted to be worn on the user's back or shoulders and means to attach the heating device to the frame.

17. A heating device for a container of a liquid pharmaceutical product contained within a glass container, the heating device comprising a rigid, thin-walled housing defining an openable chamber for receiving the container, the housing including an open end, a closed end, and a closure member operable for opening and closing of the housing for access to the chamber, a heat source in the chamber comprising a hermetically sealed package containing a super-cooled metal salt fluid or liquid and an actuator for activating the super-cooled metal salt to produce heat, and wherein the actuator is positioned so as to be accessible through the open end when the container is received within the heat source and the housing is open.

* * * * *